(12) United States Patent
Ammirati (10) Patent No.: US 7,706,873 B2
(45) Date of Patent: Apr. 27, 2010

(54) SYSTEM AND METHOD FOR CONTROLLED DELIVERY OF A THERAPEUTIC AGENT TO A TARGET LOCATION WITHIN AN INTERNAL BODY TISSUE

(76) Inventor: Mario Ammirati, 2020 Walnut St. #23J, Philadelphia, PA (US) 19103

(*) Notice: Subject to any disclaimer, the term of this patent is extended or adjusted under 35 U.S.C. 154(b) by 1407 days.

(21) Appl. No.: 10/839,326

(22) Filed: May 5, 2004

(65) Prior Publication Data
US 2005/0251024 A1 Nov. 10, 2005

(51) Int. Cl.
*A61N 1/30* (2006.01)

(52) U.S. Cl. .............. 604/20; 604/890.1; 604/891.1; 604/288.01; 604/501; 604/502; 604/503; 604/504

(58) Field of Classification Search .............. 604/890, 604/891.1, 19–20, 93.01, 288.01, 501–503, 604/506, 272; 435/173.6; 600/411, 407, 600/423, 427, 433
See application file for complete search history.

(56) References Cited

U.S. PATENT DOCUMENTS

| | | | |
|---|---|---|---|
| 3,923,060 A * | 12/1975 | Ellinwood, Jr. | 604/891.1 |
| 4,411,648 A * | 10/1983 | Davis et al. | 604/21 |
| 4,722,726 A | 2/1988 | Sanderson et al. | |
| 5,232,441 A | 8/1993 | Stephen et al. | |
| 5,236,413 A | 8/1993 | Feiring | |
| 5,256,141 A | 10/1993 | Gencheff et al. | |
| 5,423,744 A | 6/1995 | Gencheff et al. | |
| 5,499,971 A | 3/1996 | Shapland et al. | |
| 5,607,691 A | 3/1997 | Hale et al. | |
| 5,914,126 A | 6/1999 | Li et al. | |
| 6,041,252 A | 3/2000 | Walker et al. | |
| 6,083,190 A | 7/2000 | Gyory et al. | |
| 6,090,095 A | 7/2000 | McNichols et al. | |
| 6,219,577 B1 * | 4/2001 | Brown et al. | 604/20 |
| 6,278,895 B1 * | 8/2001 | Bernard | 604/20 |
| 6,328,728 B1 | 12/2001 | Holladay et al. | |
| 6,394,994 B1 | 5/2002 | Vilambi et al. | |
| 6,491,684 B1 | 12/2002 | Joshi et al. | |
| 6,520,950 B1 * | 2/2003 | Hofmann et al. | 604/503 |
| 6,522,918 B1 | 2/2003 | Crisp et al. | |
| 6,553,253 B1 | 4/2003 | Chang | |
| 6,582,416 B2 | 6/2003 | Tapper | |
| RE38,341 E | 12/2003 | Henley | |
| 6,699,282 B1 | 3/2004 | Sceusa | |
| 6,912,417 B1 * | 6/2005 | Bernard et al. | 604/20 |
| 6,972,013 B1 * | 12/2005 | Zhang et al. | 604/501 |
| 7,022,071 B2 * | 4/2006 | Schaupp et al. | 600/309 |
| 2002/0099356 A1 | 7/2002 | Unger et al. | |
| 2003/0018294 A1 | 1/2003 | Cox | |
| 2003/0083607 A1 | 5/2003 | Bobo, Jr. | |
| 2003/0097121 A1 | 5/2003 | Jolly et al. | |

(Continued)

*Primary Examiner*—Nicholas D Lucchesi
*Assistant Examiner*—Quynh-Nhu H Vu
(74) *Attorney, Agent, or Firm*—The Belles Group, PC (57) ABSTRACT

A method and system for the localized delivery of therapeutic agents to internal body tissues, especially the brain. In one aspect the invention is a method of delivering a therapeutic agent to a target location within an internal body tissue, the method comprising: charging the therapeutic agent; providing a plurality of polarizable microcatheters surrounding the target location; delivering the charged therapeutic agent between the microcatheters; and polarizing the microcatheters thereby generating an electrical field between the microcatheters that moves the charged therapeutic agent throughout the target location. In another aspect the invention is a system for carrying out the method.

19 Claims, 3 Drawing Sheets

U.S. PATENT DOCUMENTS

| | | |
|---|---|---|
| 2003/0147812 A1 | 8/2003 | Ueberle |
| 2003/0153821 A1* | 8/2003 | Berner et al. ............... 600/345 |
| 2003/0183683 A1 | 10/2003 | Stewart |
| 2003/0191426 A1 | 10/2003 | Lerner et al. |
| 2003/0195403 A1* | 10/2003 | Berner et al. ............... 600/347 |
| 2003/0199449 A1 | 10/2003 | Tarcha et al. |
| 2004/0018486 A1* | 1/2004 | Dunn et al. .................... 435/4 |
| 2006/0079841 A1* | 4/2006 | Duff et al. .................... 604/116 |
| 2006/0241548 A1* | 10/2006 | Fukuta et al. ................. 604/20 |

* cited by examiner

SYSTEM AND METHOD FOR CONTROLLED DELIVERY OF A THERAPEUTIC AGENT TO A TARGET LOCATION WITHIN AN INTERNAL BODY TISSUE

FIELD OF THE INVENTION

The present invention is related generally to systems and methods of delivering therapeutic agents to internal body tissues, and specifically to systems and methods of delivering therapeutic agents using electrical fields.

BACKGROUND OF THE INVENTION

The controlled and accurate delivery of therapeutic drugs to target locations, such as tumors, or other target areas, within tissues of the internal body has long been a goal in the medical industry. However, physiological variables and barriers often prohibit delivery of a therapeutic agent to the target location in optimal concentrations or in a systematic controlled manner. In other instances, the internal body tissue that encompasses the target location can not be subjected to substantial physical trauma, thereby limiting and/or prohibiting direct delivery of the therapeutic agent to the target location itself.

Drug delivery problems are especially problematic in the brain because of the susceptibility of the brain to permanent damage from physical trauma. Conditions/diseases involving the brain rarely involve other areas of the body. In fact, many brain conditions/diseases are rooted in malfunction of selective areas within the brain itself, such is the case for example in stroke, head injury, brain tumors, and many psychotic disorders. Yet, despite the fact that brain conditions/diseases are either localized to the brain or even to a small part of the brain, treatment of these diseases/conditions is predicated on the systemic administration of therapeutic agents to the entire body, for example, through oral, intravenous, or intra-arterial introduction into the circulatory system.

However, many brain diseases/conditions are treated with therapeutic agents that when systematically delivered to the body in quantities to provide the target location with a concentration of the agent to be curative are toxic to other areas of the body or to healthy parts of the brain. Thus, the systemic administration of therapeutic agents to the entire body to treat a brain disease/condition is not possible or less than optimal due to side effects resulting from the drugs reaching other areas of the body or parts of the brain not affected by the disease.

Drug delivery problems to locations in the brain are further complicated by the presence of the blood-brain-barrier. The blood-brain-barrier is an anatomical and physiological barrier that prevents the entry of many charged substance into the brain, thereby limiting the type of therapeutic agents that are used in the treatment of brain pathologies to non-charged (i.e., non-polarized) agents.

Localized delivery of drugs to the brain has been attempted using wafers impregnated with drugs, or through microcatheters delivering drugs using convection enhanced techniques. However these attempts have been largely unsuccessful due to the limited distribution of the therapeutic agent within the brain. Typically, the therapeutic agent will travel only a few millimeters away from its delivery location and in a non controllable fashion. Thus, there is a need for a system and method that can deliver therapeutic agents to target locations within the brain (and other tissues of the body) in a controlled and accurate manner.

DISCLOSURE OF THE INVENTION

It is therefore an object of the present invention to provide a system and method for delivering a therapeutic agent to a target location within an internal body tissue.

A further object of the present invention is to provide a system and method for delivering a therapeutic agent to a target location within an internal body tissue in a more controlled and/or accurate manner.

Another object of the present invention is to provide a system and method for delivering a therapeutic agent to a target location within the brain.

Still another object of the present invention is to provide a system and method for delivering a therapeutic agent to a target location within an internal body tissue to treat a disease/condition.

Yet another object is to provide a system and method for delivering a therapeutic agent to a target location within an internal body tissue that reduces physical damage to the body tissue.

A still further object is to provide a system and method for delivering a therapeutic agent to a target location within an internal body tissue that is less intrusive to the patient.

It is also an object to provide a system and method for delivering a therapeutic agent to locations within an internal body tissue that are difficult to treat.

Another object is to provide a system and method for delivering a therapeutic agent to a target location within the brain to treat brain diseases and/or conditions, including brain tumors, viral infections, HIV-related neurological diseases, stroke, head injury, neuro-degenerative diseases, and psychotic disorders.

These and other objects are met by the present invention, which in one aspect is a method of delivering a therapeutic agent to a target location within an internal body tissue, the method comprising: charging the therapeutic agent; providing a plurality of polarizable microcatheters surrounding the target location, delivering the charged therapeutic agent to a delivery location between the polarizable microcatheters; and polarizing the microcatheters thereby generating an electrical field between the microcatheters that moves the charged therapeutic agent back and forth in a controlled fashion so as to achieve the planned therapeutic agent concentration for a desired time within the target, thereby generating the desired therapeutic effect. The delivery location can be in/around the target location. In order to effectuate the desired movement of the charged therapeutic agent within the tissue, the electrical field is preferably adjustable/changeable. In one embodiment, the electrical field is adjusted/changed to move the charged therapeutic agent back and forth in a controlled fashion so as to achieve a desired concentration of the therapeutic agent in the target location for a desired time, thereby generating a desired therapeutic effect.

The plurality of polarizable microcatheters can be polarized through the use of an electrolytic solution or electrodes that are in turn coupled to a variable voltage power source, such as a battery, and activating the power source. Whether a specific polarizable microcatheter is charged negatively or positively depends on the location of that microcatheter with respect to the target location and the charge of the therapeutic agent. The number, position, and charge of the polarizable microcatheters that are provided to surround the target location can be determined through computer-based three-dimensional simulation.

When using simulation procedures, the target location can be identified using magnetic resonance imaging. The target location can then be simulated in three dimensional space using a computer based system and the effects of the electrical field on the charged therapeutic agent can be simulated and observed to determine the amount of the therapeutic agent and the appropriate electrical field needed to achieve the desired concentration of the therapeutic agent for a desired time within the target location.

The charged therapeutic agent can be delivered from a reservoir to the delivery location using one or more open end microcatheters (i.e., delivery microcatheters). Moreover, the polarity of one or more of the polarizable microcatheters can be switched to manipulate the direction of the movement of the charged therapeutic agent within the tissue. The strength of the electrical field can also be adjusted to control the rate of movement of the charged therapeutic agent to within the tissue. It also preferable to control the rate of delivery of the charged therapeutic agent from the reservoir. This can be accomplished through the use of a flow rate controller, such as a valve or a micro-pump.

In order to ensure that the proper concentration of the therapeutic agent is reaching the target location, the concentration of the charged therapeutic agent in the subject tissue can be measured at certain points in/around the target location. The concentration of the charged therapeutic agent can be measured using a variety of techniques, such as a microdialysis technique. The measured concentration can be compared with a desired concentration. If it is determined that the measured concentration indicates that the concentration of the charged therapeutic agent within the target location is not approximately equal to the desired concentration, the delivery of the charged therapeutic agent to the target location can be adjusted accordingly. This can be done by adjusting the strength of the electrical field, by switching polarity of one or more of the polarizable microcatheters, and/or by adjusting the rate of delivery of the charged therapeutic agent to the delivery location from the reservoir.

The method of the present invention is preferably used to deliver the charged therapeutic agent to the brain. In this embodiment, the method will include the steps of diagnosing a patient with a brain disease/condition, identifying the affected area of the brain causing the brain disease/condition, wherein the affected area is the target location, identifying a therapeutic agent that will treat the diagnosed condition or disease, and supplying the therapeutic agent to the affected part of the brain in sufficient quality. The invention can be used to treat brain diseases/conditions such as HIV-related neurological disease, stroke, head injuries, neuro-degenerative diseases, tumors, psychotic disorders, or viral infections.

The delivery location of the therapeutic agent is preferably within the internal body tissue itself. The microcatheters can be implanted within the internal body tissue for use over an extended period of time and for different therapy sessions.

In another aspect, the invention is a system for delivering a therapeutic agent to a target location within an internal body tissue, the system comprising: a plurality of microcatheters implanted in the internal body tissue surrounding the target location, the microcatheters containing polarization means; a reservoir of a charged therapeutic agent; means to deliver the charged therapeutic agent from the reservoir to a delivery location between the microcatheters; means to activate the polarization means; and wherein the microcatheters are oriented so that when the polarization means are activated, an electrical field is generated between the microcatheters that drives the charged therapeutic into the target location. The delivery location can be in/around the target location. The electrical field can be adjusted/changed to achieve a desired concentration of the therapeutic agent in the target location for a desired time, thereby generating a desired therapeutic effect.

The system preferably comprises a means for measuring the concentration of the charged therapeutic agent at a point between the microcatheters. The concentration can be measured using a microcatheter adapted to use a microdialysis technique. It is further preferable that the system comprise a means to control flow rate of the charged therapeutic agent from the reservoir to the delivery location, such as a valve. The delivery means can be a microcatheter and the means to activate the polarization means can be a variable power source. In this embodiment, the variable power source will be electrically coupled to the polarization means, which can be an electrolytic solution or an electrode.

The system also preferably comprises means to switch the polarity of one or more of the polarization means of the microcatheters to manipulate direction of movement of the charged therapeutic agent within the volume, such as switch.

DETAILED DESCRIPTION OF THE DRAWINGS

An embodiment of the present invention will now be described in detail. Regarding delivering therapeutic agents to the brain, the present invention can be used to treat a variety of brain diseases/conditions, including but not limited to brain tumors, psychotic disorders, HIV-related neurological infections, stroke, head injuries, neuro-degenerative diseases (e.g., Alzheimer's and Parkinson's). Each of these diseases/conditions will be discussed briefly.

The incidence of brain tumors is approximately 20/100,000 per year. Current treatments for brain tumors include resection, radiation, and chemotherapy. Treatment success rates vary by tumor type, but are generally low, especially for malignant brain tumors, and the risk of side effects or disability is high. The most common brain tumors are of glial cell origin and are associated with an extremely poor prognosis despite multi-modality approaches. Their average survival is less than two years even after surgical resection and extensive treatments with high dose radiation and chemotherapy. It is recognized that improvements in treating primary and secondary brain tumors are needed. In one embodiment, the present invention addresses these needs.

It is estimated that about 2.5 million patients are afflicted with schizophrenia in the United States and about 250 million worldwide. Adherence to prescribed drug regimens is recognized as a significant treatment obstacle in the schizophrenic population. Although it is estimated that 50% of patients in the U.S. are either untreated or under treated, the aggregated sales of antipsychotic medications in 2000 exceeded $5.7 billion. Schizophrenia is recognized as a disease affecting specific areas of the brain that are being continuously better defined. Application of localized drug delivery, according to an embodiment of the present invention, for this and other major psychoses may be very beneficial in medicating and controlling the symptoms of these conditions.

Anti-viral nucleosides are water-soluble, polar substances and do not easily cross the blood-brain barrier. Typically, less than 1% of intravenously administered zidovudine (AZT) will enter the brain. This is a critical issue in developing new treatment approaches to brain viral infections, including HIV-related neurological disease. Controlled local delivery of therapeutic substances, according to one embodiment of the present invention, could greatly enhance the efficacy of HIV-related brain conditions. Stroke, head injuries, neuro-degenerative diseases (Alzheimer's and Parkinson's disease) are example of some other brain diseases that could benefit from the present invention.

Figure 2:
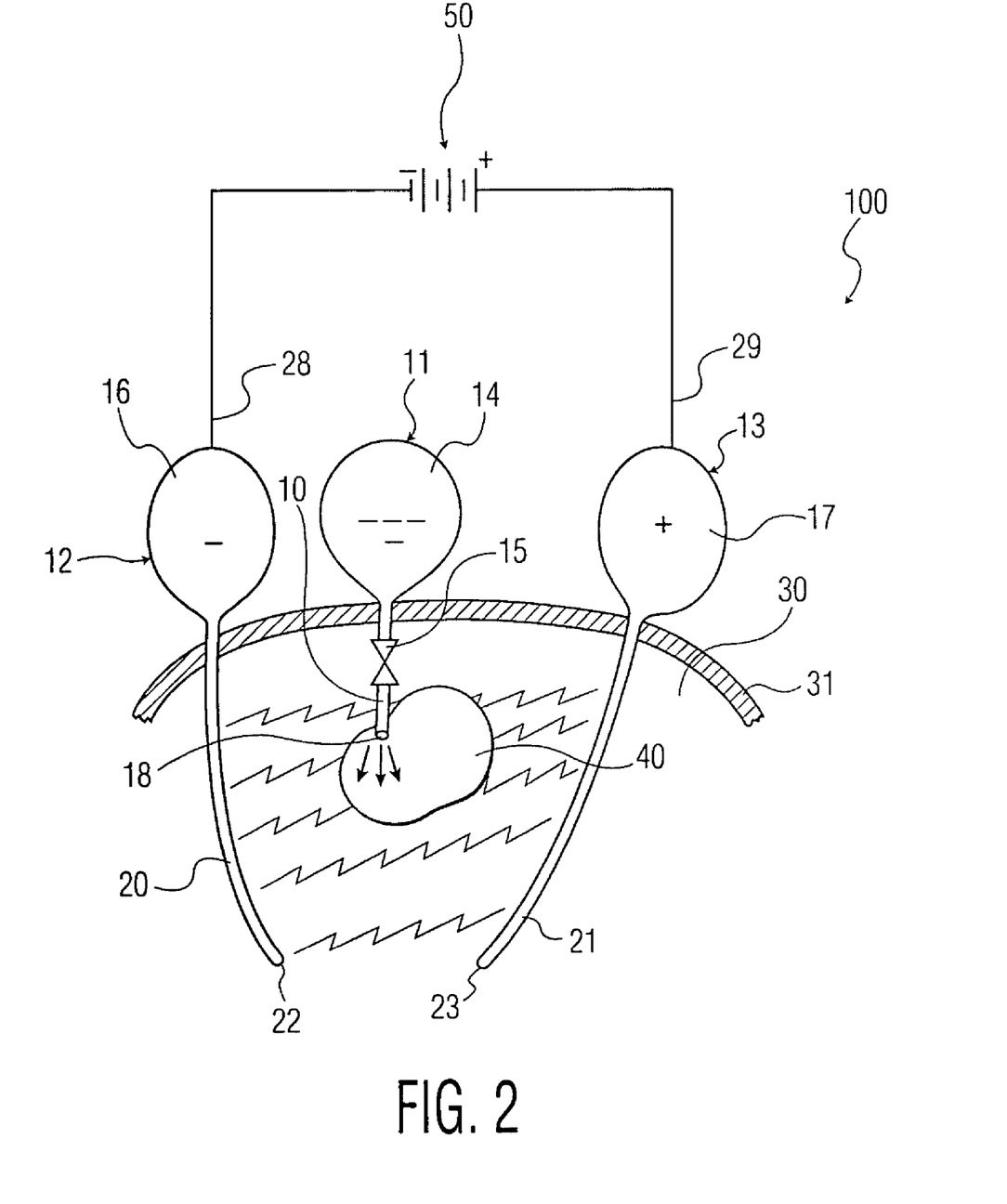
FIG. 2 is a cross-sectional schematic of a drug delivery system according to an embodiment of the present invention positioned within the brain of a patient and connected to a variable voltage battery.

Referring to FIG. 2, drug delivery system 100 is schematically illustrated delivering charged therapeutic agent 14 to a target location 40 within brain 30 of a patient according to an embodiment of the present invention. Drug delivery system 100 comprises polarizable microcatheters 20, 21, delivery microcatheter 10, reservoirs 11-13, and variable voltage battery 50.

Microcatheter 20 is fluidly coupled to reservoir 12. Microcatheter 21 is fluidly coupled to reservoir 13. Both reservoirs 12, 13 are filled with electrolytic solutions 16 and 17 respectively (i.e., a fluid that can carry an electric current/charge). Electrolytic solutions 16 and 17 can be the same type of solution or can be different types. Microcatheter 20 has a closed end 22 and is filled with electrolytic solution 16 from reservoir 12. Similarly, microcatheter 21 has a closed end 23 and is filled with electrolytic solution 17 from reservoir 13. Both microcatheters 20 and 21 extend through skull 31 of the patient and into brain 30, surrounding target location 40.

Delivery microcatheter 10 is fluidly coupled to reservoir 11. Reservoir 11 is filled with negatively charged therapeutic agent 14. The exact therapeutic agent used is determined by the brain disease/condition that is to be treated with the medical procedure. The therapeutic agent can be an existing drug or a later developed drug. Additionally, the therapeutic agent can be charged either negatively or positively by known methods. It is important to choose therapeutic agents and/or charging methods where the curative/treatment characteristics are not altered by charging. Delivery microcatheter 10 has an open end 18 and comprises valve 15 operably coupled thereto.

When valve 15 is open, the charged therapeutic agent 14 flows from reservoir 11, through the length of delivery microcatheter 10 and into the target location 40 through open end 18. When valve 15 is closed, fluid flow of charged therapeutic agent 14 through delivery microcatheter 10 is prohibited. FIG. 2 illustrates valve 15 in the open position. Additionally, valve 15 can be of the variable type that allows the flow rate of charged therapeutic agent 14 to be adjustable and controllable. Optionally, the flow rate allowed by valve 15 can be automatically controlled by coupling valve 15 to a properly programmed microprocessor or controller (not illustrated). Valve 15 can be a pinch-type valve or any other type of valve.

Delivery microcatheter 10 extends through skull 31 and open end 18 is located at a position between polarizable microcatheters 20, 21 and into target location 40. As such, the negatively charged therapeutic agent 14 is delivered to target location 40 when valve 15 is open. While delivery microcatheter 10 pierces the skull 31 between where microcatheters 20, 21 pierce the skull 31, this is not necessary, so long as the charged therapeutic agent is delivered at a location between microcatheters 20, 21. While the therapeutic agent is illustrated as being delivered via a microcatheter, other means can be used such as a needle. Additionally, while the charged therapeutic agent is shown to be delivered into the target location and through a single delivery microcatheter, the charged therapeutic agent may be delivered to the brain at apposition around the target location and/or through multiple delivery microcatheters.

Drug delivery system 100 further comprises variable voltage battery 50. The negative lead 28 of battery 50 is electrically coupled to electrolytic solutions 16 in reservoir 12. Similarly, the positive lead 29 of battery 50 is coupled to electrolytic solutions 17 in reservoir 13. When battery 50 is activated, electrolytic solution 17 that fills reservoir 13 and microcatheter 21 becomes polarized with a positive charge. At the same time, electrolytic solution 16 that fills reservoir 12 and microcatheter 20 becomes polarized with a negative charge. Supplying sufficient voltage from battery 50 results in the polarization of microcatheters 20, 21 so that an electrical field is generated therebetween (indicated by the squiggly lines). The strength of the electrical field can be varied by varying the voltage of battery 50. Additionally, the polarity (i.e., negative or positive charge) of either microcatheter 20, 21 can be changed during use, or before use, through the use of an appropriate electrical switch (not illustrated) installed in the circuitry.

Because therapeutic agent 14 is charged (i.e., polarized) the electrical field generated by microcatheters 20, 21 will force movement of the therapeutic agent within brain 30. More specifically, because the therapeutic agent 14 is negatively charged, the electrical field will drive the delivered therapeutic agent 14 from the delivery location adjacent open end 18 to the right, in a direction toward positively polarized microcatheter 21 and away from negatively polarized microcatheter 20. When the polarity of polarizable microcatheters 20 and 21 is switched the movement will be in the opposite direction. The position of microcatheters 20, 21 and the delivery location of therapeutic drug 14 is established so that the electrical field forces the delivered therapeutic agent throughout the entire target location 40. Moreover, while an electrolytic solution is preferably provided in the microcatheters to facilitate polarization, other means can be used, such as a thin electrode/wire positioned therein.

While FIG. 2 illustrates a two-dimensional schematic using only two microcatheters 20, 21 defining an area, a plurality of microcatheters may be implanted in the tissue of interest in a three dimensional orientation. Such a three dimensional arrangement is illustrated in FIG. 1.

Figure 1:
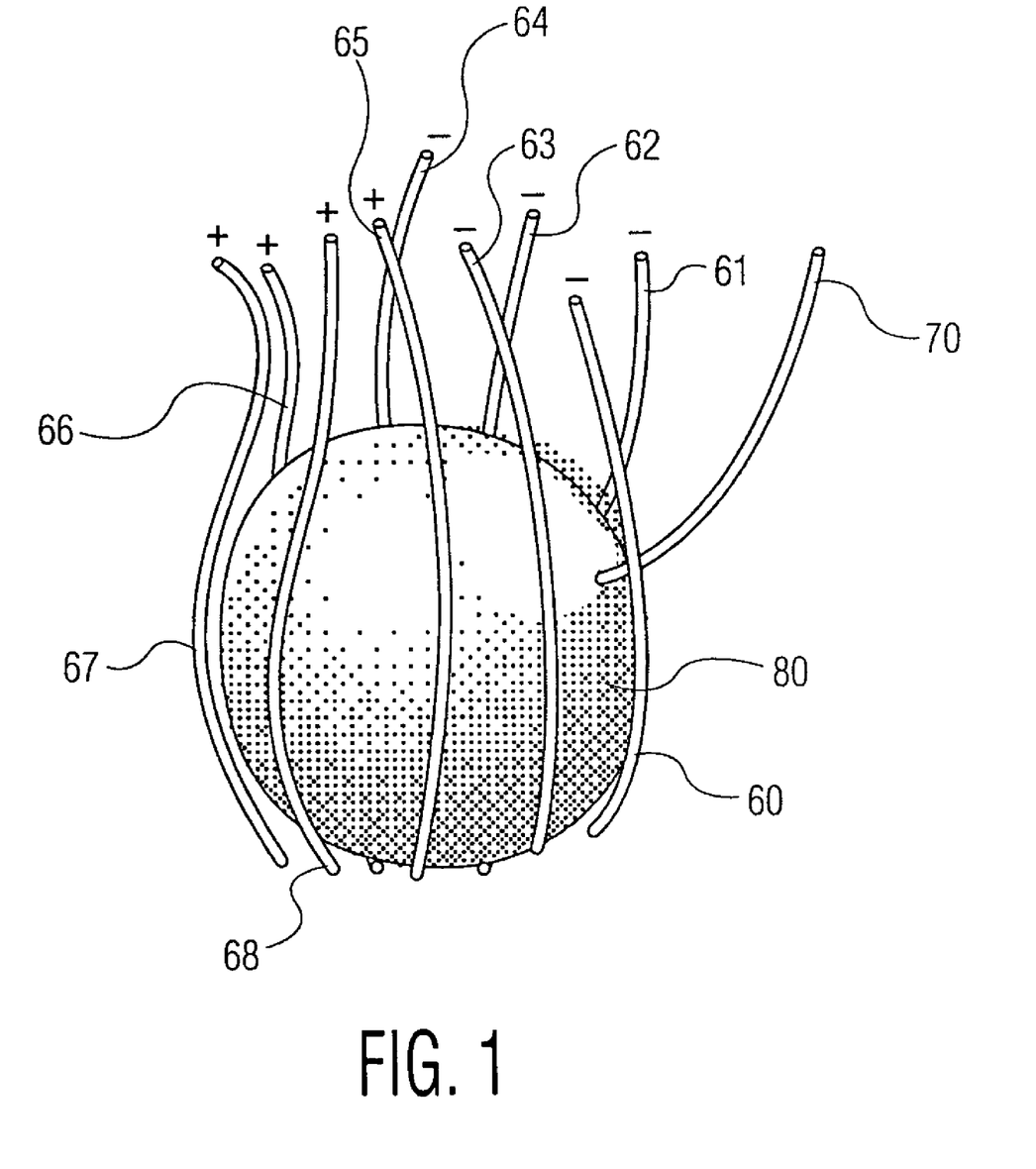
FIG. 1 is perspective view of a drug delivery system according to an embodiment of the present invention wherein an array of polarized microcatheters surrounds a volume encompassing a target location.

Referring to FIG. 1, a plurality of microcatheters 60-68 are provided in the tissue (or surrounding the tissue) so as to surround a volume 80 encompassing the target location. Volume 80 is illustrated as a sphere for convenience but can be any shape or size. Microcatheters 60-64 are polarized with a negative charge in a manner similar to that discussed above with respect to microcatheter 20. Microcatheters 65-68 are polarized with a positive charge in a manner similar to that discussed above with respect to microcatheter 21. When so charged, an electrical field is generated between the microcatheters 60-68 and within volume 80. Delivery microcatheter 70 delivers a negatively charged therapeutic agent 90 to a delivery location within volume 80. The electrical field forces the charged therapeutic agent 90 into the target location within volume 80. The polarity of any of the microcatheters 60-68 can be changed during use to appropriately control the direction of movement of the therapeutic agent 70 within volume 80. Additionally, the strength of the electrical field generated can also be adjusted during use, as discussed above, to control the rate of movement of the therapeutic agent 90 within the volume 80. The position, number, and polarity of the microcatheters used in any procedure can be predetermined through computer simulation. The exact voltage and polarity required for any given situation will depend on the tissue being treated, the distance between the polarized catheters, the therapeutic agent being delivered, and the mechanics and number of the microcatheters used.

Additionally, any of the polarized microcatheters (or a separate microcatheter) can be adapted to measure the concentration of the therapeutic agent in the subject tissue at a given location. Preferably, concentration will be determined using a microdialysis technique. In this embodiment, it is possible to couple the concentration measuring device to a properly programmed microprocessor or controller (not illustrated). A desired concentration value can be stored in a memory and the controller can compare the measured concentration to the desired concentration. By coupling the controller/microprocessor to the valve, the battery, and/or the switch, the delivery variables can be automatically adjusted to achieve the desired concentration. The delivery variables that can be adjusted include the rate of the delivery of the therapeutic agent through the delivery microcatheter by adjusting the valve, the rate at which the therapeutic substance is forced into the target location by adjusting the strength the electrical field, and the direction of movement of the therapeutic substance between the microcatheters by switching the polarity of any one or more of the microcatheters.

Using one or a combination of the methods above, the electrical field can be adjusted/changed to maintain so as to achieve a desired concentration of the therapeutic agent in the target location (and volume 80 if so desired) for a desired time, thereby generating a desired therapeutic effect. This can be achieved by moving the charged therapeutic agent back and forth within volume 80 in a controlled fashion using changes in polarity.

Figure 3:
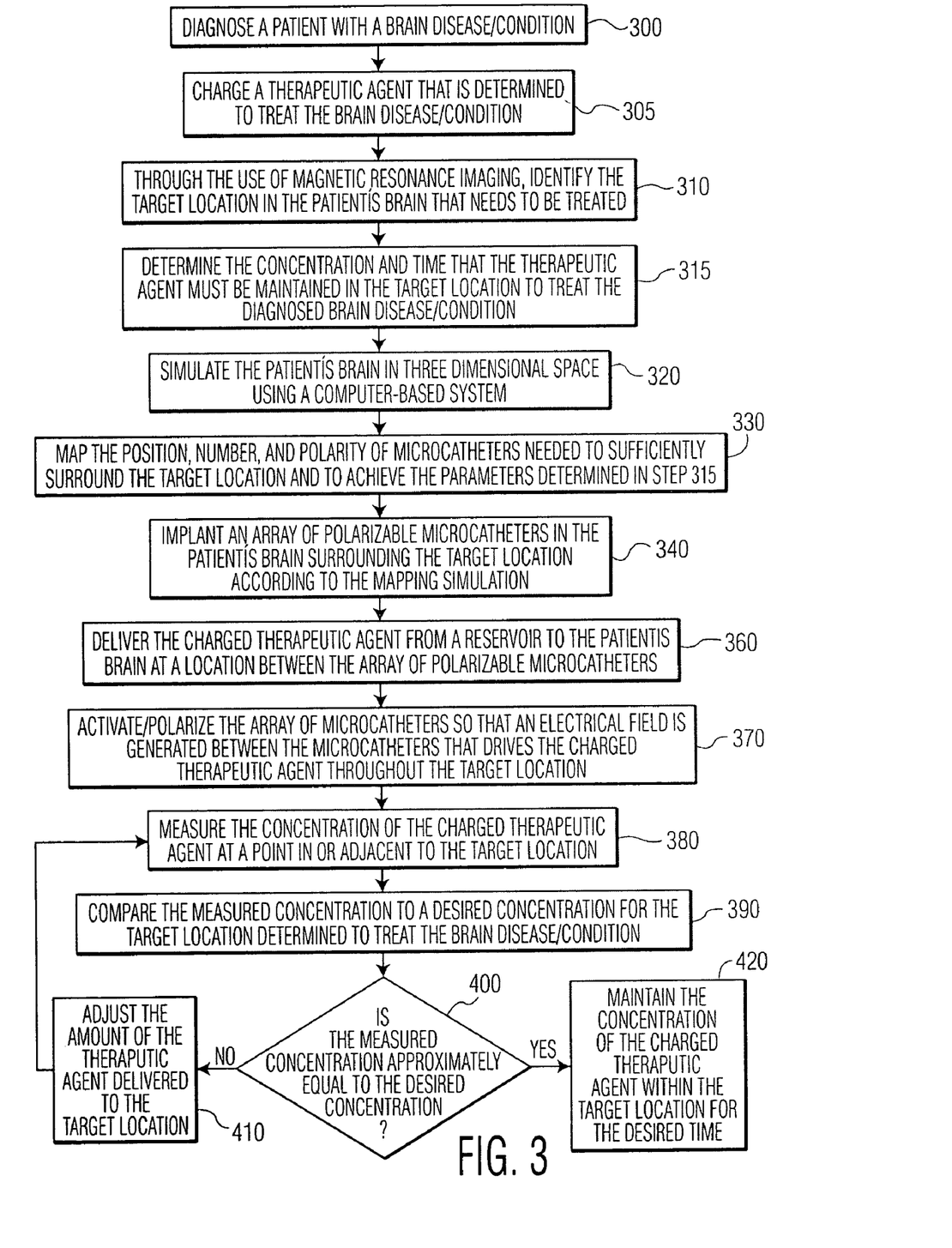
FIG. 3 is a block diagram of a method of delivering a therapeutic agent to a target location within the brain according to an embodiment of the present invention.

FIG. 3 is a block diagram of a method of delivering a therapeutic agent to the brain of a patient according to an embodiment of the present invention. The method of FIG. 3 will be described in detail with respect to the drug delivery system 100 of FIG. 2.

At step 300, a patient is diagnosed with a specific brain disease/disorder, such as, for example, one of the brain diseases/conditions mention above. At step 305 an appropriate therapeutic agent 14 that will treat the diagnosed brain disease/condition is identified and charged (i.e. given either a positive or a negative electrical charge). Once the patient is diagnosed with a specific brain disease/condition, the affected area of the patient's brain 30 is identified using conventional methods, such as magnetic resonance imaging ("MRI") or cat scan procedures, completing step 310. For purposes of example, the affected area is the target location 40. As used herein, the target location 40 is the area/volume to which one desires to deliver the therapeutic agent 14. The target location can be a specific lobe of the brain, a portion of a lobe of the brain, or any general area/volume within the brain. The target location can be any size or shape. At step 315 the concentration in the target and the time this concentration must be maintained in order to achieve the desired therapeutic effect are computed.

The patient's brain 30 is then simulated in three dimensional space using a computer based system using programs such as VoxelView and VoxelMath (produced by Vital Images, Inc.), completing step 320. The three dimensional simulation of the brain will indicate the target location 40 within the brain 30. Using the three dimensional simulation of the brain 30, the number, position, and polarity of the microcatheters needed to surround the target location and perform the desired functions is mapped, completing step 330. The polarity switches and the strength/duration of the electrical field needed to achieve the parameters calculated in step 315 are also determined in step 330. The number, position, and polarity of the microcatheters needed in any procedure will depend on a variety of factors, including the type of internal tissue being treated, the identity of the therapeutic agent being used, the size and shape of the target location, and the type of microcatheters being used.

Once the number, position, and desired polarity of the microcatheters needed for the procedure is determined, the implanting procedure is performed. At step 340, the microcatheters, including microcatheters 20 and 21 (FIG. 2), are implanted in the patient's brain 30 according to the three dimensional computer map. For ease of discussion, only microcatheters 20, 21 will be discussed with the understanding that the invention is not limited to any specific number of microcatheters. The implanted microcatheters 20, 21 are filled with electrolytic solutions 16, 17 respectively and surround the target location 40.

The therapeutic agent 14, selected in step 305, is then delivered to target location 40 in the patient's brain 30 via delivery microcatheter 10, completing step 360. At step 370, battery 50 is activated, thereby sending an electrical current into electrolytic solutions 16, 17 and polarizing microcatheters 20, 21. As a result of microcatheters 20, 21 being polarized, an electrical field is generated between microcatheters 20, 21 that drives the delivered therapeutic agent 14 throughout the whole target 40. The polarity of microcatheters 20, 21 will be switched as necessary to drive the delivered therapeutic agent 14 throughout the whole target 40 and to maintain the delivered therapeutic agent 14 within the target location 40 for the desired time.

At step 380, the concentration of the charged therapeutic agent 14 in the brain tissue 30 is measured at a point at or near the target location 40. The concentration measurement is preferably taken with a microcatheter (not illustrated) that is adapted to measure the concentration using a microdialysis technique. The device used to measure concentration can be operably coupled to a properly programmed microprocessor or controller. Signals indicative of the measured concentration are transmitted to the controller for analysis. Specifically, the controller can be programmed to compare the measured concentration to a predetermined desired concentration that is stored in a controller memory, completing step 390.

The controller performs decision block 400 and determines whether the measured concentration is approximately equal to the desired concentration. If the answer is NO, step 410 is performed and the delivery of the charged therapeutic agent 14 to the target location 40 is adjusted to achieve the desired concentration at the measuring position. The delivery of the charged therapeutic agent 14 to the target location 40 can be performed by a variety of ways, including: (1) adjusting the delivery rate of the therapeutic agent 14 from the reservoir 11 by adjusting valve 15; (2) adjusting the direction of movement of the delivered therapeutic agent 14 within the brain tissue 30 by switching the polarity of one or more of the microcatheters, including microcatheters 20, 21, to; and/or (3) changing the strength of the electrical field by varying the voltage of battery 50. The adjustments can be made manually or automatically. In an automated system, the controller/microprocessor will be operably coupled to valve 15, variable voltage battery 50, and/or switches located in the circuitry.

Upon completion of step 410, the process returns to step 380 and completes step 380-400 until the answer at decision block 400 is YES. The concentration can be measured continuously or at specified time intervals. If the answer at decision block 400 is YES, step 420 is performed and the therapeutic agent 14 is maintained inside the target location 40 at the desired concentration for the desired length of time. In an alternative embodiment, if the answer at decision block 400 is YES, steps 380-400 can still be repetitively performed to ensure that the desired concentration level is maintained.

While the invention has been described and illustrated in sufficient detail that those skilled in this art can readily make and use it, various alternatives, modifications, and improvements should become readily apparent without departing from the spirit and scope of the invention. Specifically, while the illustrated embodiment of the invention describes the delivery of a therapeutic agent to the brain, the invention is not so limited and can be used to deliver a therapeutic agent to any internal body tissue.

What is claimed is:

1. A method of delivering a therapeutic agent to a target location within an internal body tissue, the method comprising:
   charging the therapeutic agent;
   implanting at least a portion of a plurality of polarizable microcatheters within the internal body tissue to surround the target location, the polarizable microcatheters having closed ends and filled with a fluidic electrolytic solution;
   delivering the charged therapeutic agent to a delivery location between the microcatheters; and
   polarizing the electrolytic solution within the microcatheters thereby generating an electrical field between the microcatheters that moves the charged therapeutic agent throughout the target location.

2. The method of claim 1 wherein the delivery location is within or adjacent to the target location.

3. The method of claim 1 wherein the internal body tissue is the brain.

4. The method of claim 1 wherein the charged therapeutic agent is delivered to the delivery location using an open end microcatheter.

5. The method of claim 1 further comprising switching polarity of one or more of the polarizable microcatheters to manipulate direction of movement of the charged therapeutic agent.

6. The method of claim 1 further comprising varying strength of the electrical field generated by the polarizable microcatheters to control rate of movement of the charged therapeutic agent.

7. The method of claim 1 further comprising:
   identifying the target location using magnetic resonance imaging; and
   simulating the target location in three dimensional space using a computer based system.

8. The method of claim 7 wherein the number and position of the polarizable microcatheters is determined using the simulated target location on the computer based system.

9. The method of claim 1 further comprising measuring concentration of the charged therapeutic agent at a point in the internal body tissue between the polarizable microcatheters.

10. The method of claim 9 further comprising adjusting rate of movement or direction of movement of the charged therapeutic agent within the internal body tissue based on the concentration measurement.

11. The method of claim 9 wherein the measuring of the concentration of the charged therapeutic agent is accomplished using a microdialysis technique.

12. The method of claim 1 wherein the delivery of the charged therapeutic agent is accomplished in a rate controlled manner by a delivery system comprising a reservoir of the charged therapeutic agent and a valve.

13. The method of claim 1 further comprising:
   diagnosing a patient having a brain disease or condition;
   identifying an affected area of the brain causing the brain disease or condition, wherein the target location is the affected area;
   choosing the therapeutic agent to treat the brain disease or condition; and supplying the charged therapeutic agent to the target location in a quantity to treat the diagnosed brain disease or condition.

14. The method of claim 13 wherein the internal body tissue is the brain and the charged therapeutic agent is selected to treat viral infections, HIV-related neurological disease, stroke, head injuries, neuro-degenerative diseases, tumors, or psychotic disorders.

15. The method of claim 1 further comprising switching the polarity of the polarizable microcatheters to drive the charged therapeutic agent back and forth within the target location to maintain the charged therapeutic agent within the target location for a desired time.

16. An automated method of delivering and maintaining a therapeutic agent in a target location within an internal body tissue at a desired concentration, the method comprising:
   a) providing a system comprising a controller, a memory device storing data corresponding to the desired concentration, a battery, a plurality of polarizable microcatheters, means for measuring concentration of the therapeutic agent, wherein the controller, the memory device, the battery, the plurality of polarizable microcatheters, and the concentration measuring means are operably connected to one another;
   b) implanting the plurality of polarizable microcatheters within the internal body tissue so as to surround the target location;
   c) implanting the concentration measuring means within the internal body tissue so that concentration of the therapeutic agent in the target location can be measured;
   d) delivering the charged therapeutic agent to a delivery location between the polarizable microcatheters;
   e) polarizing the polarizable microcatheters thereby generating an electrical field between the polarizable microcatheters that moves the charged therapeutic agent throughout the target location;
   f) repetitively measuring concentration of the charged therapeutic agent within the target location with the concentration measuring means, the concentration measuring means transmitting signals indicative of the measured concentration to the controller;
   g) the controller receiving the signals and comparing the measured concentration with the desired concentration stored in the memory device; and
   h) upon determining that the measured concentration is not approximately equal to the desired concentration, the controller automatically adjusting delivery of the charged therapeutic agent to the target location until the measured concentration is approximately equal to the desired concentration.

17. The method of claim 16 wherein the adjusting delivery of the charged therapeutic agent to the target location in step h) is accomplished by the controller adjusting strength of the electrical field, switching polarity of one or more of the polarizable microcatheters, and/or adjusting rate of delivery of the charged therapeutic agent to the delivery location.

18. An automated method of treating a disease or condition comprising:
   a) identifying an affected location of tissue causing a disease or condition;

b) selecting a charged therapeutic agent to treat the diagnosed disease or condition;

c) determining a desired concentration to which the affected location must be exposed to the charged therapeutic agent to treat the disease or condition;

d) implanting a plurality of polarizable microcatheters so as to surround the affected location;

e) delivering the charged therapeutic agent to the affected location from a reservoir in a quantity sufficient to achieve the desired concentration level in the affected location;

f) polarizing the polarizable microcatheters thereby generating an electrical field between the polarizable microcatheters that moves the charged therapeutic agent throughout the affected location;

g) repetitively measuring concentration of the charged therapeutic agent in-situ within the affected location; and h) upon determining that the measured concentration is not approximately equal to the desired concentration, automatically adjusting delivery of the charged therapeutic agent to the target location until the measured concentration is approximately equal to the desired concentration.

19. The method of claim 18 wherein the tissue is brain tissue.

* * * * *